United States Patent [19]

Floyd et al.

[11] Patent Number: 4,788,010
[45] Date of Patent: Nov. 29, 1988

[54] AMINO SUBSTITUTED BENZENEPROPANOLS

[75] Inventors: David M. Floyd, Pennington; Spencer D. Kimball, East Windsor; Steven Brandt, Plainsboro, all of N.J.

[73] Assignee: E. R. Squibb & Sons, Inc., Princeton, N.J.

[21] Appl. No.: 726,549

[22] Filed: Apr. 24, 1985

[51] Int. Cl.$^4$ .................. C07C 91/16; C07C 93/08
[52] U.S. Cl. .................. 260/501.17; 250/501.10; 514/554; 514/648; 564/316; 564/358
[58] Field of Search ............ 564/316, 358, 501.17; 250/501.18; 514/554, 648

[56] References Cited

U.S. PATENT DOCUMENTS

| | | | |
|---|---|---|---|
| 3,132,179 | 5/1964 | Clarke | 564/355 |
| 3,804,899 | 4/1974 | Ebnather et al. | 564/355 X |
| 3,928,369 | 12/1975 | Berntsson et al. | 564/316 X |
| 4,058,642 | 11/1977 | Renth et al. | 564/355 X |
| 4,242,355 | 12/1980 | Nedelec et al. | 564/316 X |
| 4,259,257 | 3/1981 | Levai et al. | 564/316 X |

FOREIGN PATENT DOCUMENTS

| | | |
|---|---|---|
| 1377787 | 2/1972 | United Kingdom . |
| 105696 | 9/1983 | United Kingdom . |

OTHER PUBLICATIONS

Arzneim-Forsch, vol. 23, pp. 74–77.
S. African Journal of Chemistry, vol. 33, pp. 34–38 (1980).
S. African Journal of Chemistry, vol. 31, pp. 135–137 (1978).
Journal of Chemical Society, Perkins Transactions, vol. 1(2), pp. 191–192.
Journal of Medicinal Chemistry, vol. 25, pp. 1248–1250.
Indian Journal of Chemistry, vol. 15B, pp. 260–263 (1977).
Journal of Medicinal Chemistry, vol. 19, pp. 1270–1275 (1976).
Australian Journal Exp. Bio. Med. Sci., vol. 59, pp. 179–182.
European Journal of Pharmacology, vol. 67, pp. 85–89 (1980).

Primary Examiner—Robert V. Hines
Attorney, Agent, or Firm—Lawrence S. Levinson; Donald J. Barrack

[57] ABSTRACT

Hypotensive activity is exhibited by compounds having the formula

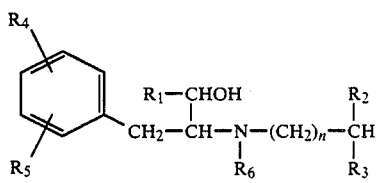

and pharmaceutically acceptable salts thereof wherein
$R_1$ is hydrogen or alkyl;
$R_2$ and $R_3$ are each independently phenyl, substituted phenyl, cycloalkyl, or $R_2$ is hydrogen and $R_3$ is heteroaryl;
$R_4$ and $R_5$ are the same or different and each is hydrogen, hydroxy, alkoxy, alkanoyl or alkyl;
$R_6$ is hydrogen or alkyl; and
n is 1, 2, 3 or 4; with the proviso that if $R_2$ and $R_3$ are each phenyl, at least one of $R_1$, $R_4$, $R_5$ and $R_6$ is other than hydrogen.

12 Claims, No Drawings

AMINO SUBSTITUTED BENZENEPROPANOLS

BRIEF DESCRIPTION OF THE INVENTION

Compounds having the formula

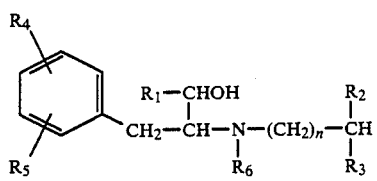

and pharmaceutically acceptable salts thereof, are useful for the treatment of hypertension. In formula I, and throughout the specification, the symbols are as defined below.

$R_1$ is hydrogen or alkyl;

$R_2$ and $R_3$ are each independently phenyl, substituted phenyl, or cycloalkyl, or $R_2$ is hydrogen and $R_3$ is heteroaryl;

$R_4$ and $R_5$ are the same or different and each is hydrogen, hydroxy, alkoxy, alkanoyl or alkyl;

$R_6$ is hydrogen or alkyl; and n is 1, 2, 3 or 4; with the proviso that if $R_2$ and $R_3$ are each phenyl, at least one of $R_1$, $R_4$, $R_5$ and $R_6$ is other than hydrogen.

Listed below are the definitions of the various terms used to describe the compounds of this invention. These definitions apply to the terms as they are used throughout the specification either individually or as part of a larger group.

The terms "alkyl" and "alkoxy", as used throughout the specification refer to both straight and branched chain groups. Those groups having 1 to 7 carbon atoms are preferred.

The term "alkanoyl", as used throughout the specification, refers to groups having the formula

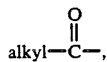

wherein alkyl is as defined above. Alkanoyl groups having 2 to 7 carbon atoms are preferred.

The term "substituted phenyl", as used throughout the specification, refers to phenyl substituted with 1, 2 or 3 groups. Exemplary substituents include alkyl, alkoxy, halogen, trifluoromethyl, alkanoylamino, and dialkylamino groups.

The term "heteroaryl", as used throughout the specification, refers to an organic radical derived from an optionally substituted heteroaromatic compound. Exemplary groups include 2-, 3- or 4-pyridinyl, 2- or 3-furanyl, 2- or 3-thienyl, 1-, 2- or 3-indolyl, 2-benzoxazolyl, 2-benzothiazolyl, 1- or 2-benzimidazolyl, 2- or 3-benzothienyl and 2- or 3-benzofuranyl, and to any of the above groups substituted with 1, 2 or 3 alkyl, alkoxy, halogen, alkylamino, dialkylamino, alkanoylamino, phenylcarbonylamino or (substituted phenyl)carbonylamino groups.

DETAILED DESCRIPTION OF THE INVENTION

The compounds of this invention can be prepared by first reacting a compound having the formula

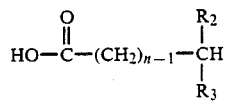

with a compound having the formula

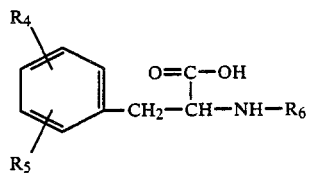

to yield the corresponding compound having the formula

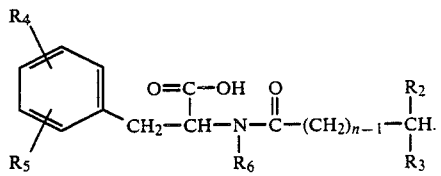

Art-recognized procedures for the formation of amides can be used for the above reaction. While compounds of formula II and III can be reacted directly, it is preferred to first prepare an acid halide (preferably the acid chloride) derivative of a compound of formula II, and then react that derivative with a compound of formula III.

Chemical reduction of a compound of formula IV yields the corresponding product of formula I wherein $R_1$ is hydrogen. Lithium aluminum hydride is the preferred chemical reducing agent.

Those compounds of this invention wherein $R_1$ is alkyl can be prepared from the corresponding compound of formula I wherein $R_1$ is hydrogen. If $R_6$ is also hydrogen, the amino group of a compound of formula I wherein $R_1$ is hydrogen is first protected with a conventional amino protecting group, e.g. a benzyloxycarbonyl group or a t-butoxycarbonylamino group, yielding a compound having the formula

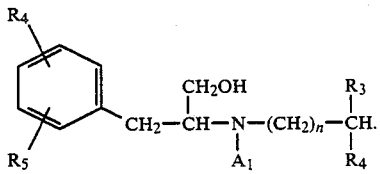

In formula V, and throughout the specification, the symbol "$A_1$" represents alkyl or a conventional amino protecting group.

The alcohol of formula V can be treated with a complex of pyridine-sulfur trioxide in the presence of a tertiary amine (e.g., triethylamine) to yield the corresponding aldehyde having the formula

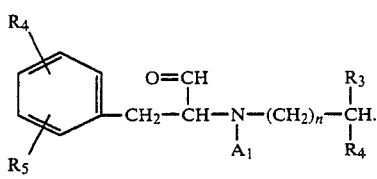

Alkylation of a compound of formula VI can be accomplished using a Grignard reagent, and yields a compound having the formula

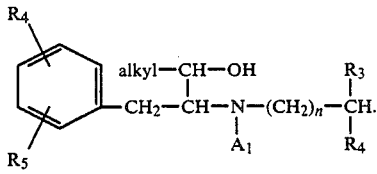

In those instances wherein $A_1$ is an amino protecting group, it can be removed from a compound of formula VII to obtain the corresponding product of formula I wherein $R_1$ is alkyl and $R_6$ is hydrogen. The conditions used to remove the amino protecting will, of course, depend on the particular protecting group present. If, for example, a benzyloxycarbonyl protecting group is used, it can be removed by catalytic hydrogenation.

Alternatively, the compounds of this invention can be prepared by first reacting a compound of formula II with a compound having the formula

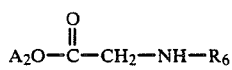

to yield the corresponding compound having the formula

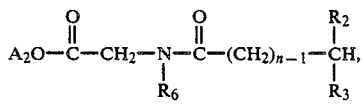

wherein $A_2$ is a carboxyl protecting group.

Treatment of a compound of formula IX with a base (e.g., lithium diisopropylamide/tetramethylenediamine) to deprotonate the compound, followed by alkylation with a compound having the formula

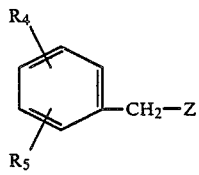

wherein Z is a leaving group such as halogen, yields the corresponding compound having the formula

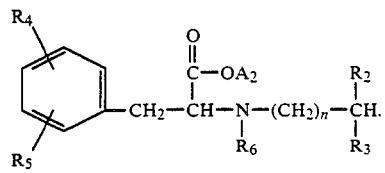

Chemical reduction of a compound of formula XI using, for example, lithium aluminum hydride as the reducing agent, yields the corresponding product of formula I wherein $R_1$ is hydrogen.

Variations of the above-described processes for preparing the compounds of this invention will be apparent to the practitioner of this invention. For example, if one (or both) of $R_4$ and $R_5$ is alkoxy, a starting material of formula III wherein $R_4$ (or $R_4$ and $R_5$) is hydroxy can be used. The hydroxy group(s) can be converted to the desired alkoxy group(s) later in the process.

The compounds of formula I form acid addition salts with inorganic and organic acids. Those acid addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate inorganic or organic acid. Illustrative are the hydrohalides, especially the hydrochloride and hydrobromide which are preferred, sulfate, nitrate, phosphate, borate, acetate, tartrate, maleate, citrate, succinate, benzoate, ascorbate, salicylate, methanesulfonate, benzenesulfonate, toluenesulfonate and the like.

In those compounds of formula I wherein $R_1$ is alkyl, different diastereomers may be prepared. These are labeled "threo" having the formula

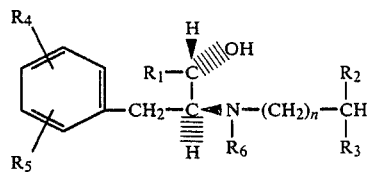

and "erythro" having the formula

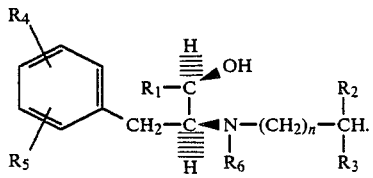

Both of these forms are included within the scope of structural formula I. The "erythro" diastereomer can be prepared using the methodology described above. The "threo" diastereomer can be prepared from the corresponding "erythro" diastereomer by first oxidizing and then chemically reducing the compound. This procedure is further illustrated in the examples presented infra.

The compounds of formula I, and the pharmaceutically acceptable salts thereof, are used for lowering the blood pressure of a mammalian host; e.g., humans. Daily doses of from about 10 milligrams to about 1.0 gram can be administered in single or divided doses. The particular daily dosage used will vary with the potency of the particular compound used and with the severity of a particular patient's hypertensive condition.

The active compounds of the present invention can be administered orally, for example, with an inert diluent or with an assimilable edible carrier, or they can be enclosed in hard or soft gelatin capsules, or they can be compressed into tablets, or they can be incorporated directly with the food of the diet. For oral therapeutic administration, the active compounds of this invention can be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations can, of course, be varied and can conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

The following examples are specific embodiments of this invention.

EXAMPLE 1

(erythro)-β-[(3,3-Diphenylpropyl)amino]-α-methylbenzenepropanol, monohydrochloride (A) α-[(1-Oxo-3,3-diphenylpropyl)amino]benzenepropionic acid To a magnetically stirred suspension of 5.00 g (22.1 mmol) of diphenylpropionic acid in 25 ml of dry dichloromethane under nitrogen was added 2.12 ml (24.3 mmol) of oxalyl chloride followed by two drops of dimethylformamide. After stirring for one hour, the solution was rotary evaporated and the residue placed under high vacuum to further remove any remaining volatiles. The resulting yellow oil was added to a solution of 3.65 g (22.1 mmol) of racemic phenylalanine in 50 ml of saturated aqueous sodium bicarbonate and 10 ml of tetrahydrofuran. The mixture was allowed to stir for three hours while maintaining the pH at 8. The mixture was then acidified to pH 2 with concentrated hydrochloric acid and partitioned between ethyl acetate and water. The ethyl acetate layer was washed with 10% aqueous hydrochloric acid, water, brine, dried over magnesium sulfate, filtered and rotary evaporated. Recrystallization of the residue from toluene gave 4.60 g of the title compound as an off-white solid, melting point 138°–140° C.

(B) β-[(3,3-Diphenylpropyl)amino]benzenepropanol, monohydrochloride

To a magnetically stirred suspension of 2.03 g (53.5 mmol) of lithium aluminum hydride in 25 ml of dry ether at 0° C. under argon was added dropwise a solution of 4.00 g (10.7 mmol) of α-[(1-oxo-3,3-diphenylpropyl)amino]benzenepropionic acid in 50 ml of 1:1 ether:tetrahydrofuran. The suspension was heated to reflux overnight, cooled to 0° C. and quenched sequentially with 2 ml of water, 2 ml of 15% aqueous sodium hydroxide, 5 ml water, and then filtered. The filtrate was shaken with 10% aqueous hydrochloric acid and the resulting white precipitate filtered and dried in vacuo to give 1.61 g of the title compound, melting point 181°–190° C.

(C) β-[[[(Phenylmethyl)oxy]carbonyl](3,3-diphenylpropyl)amino]benzenepropanol

To a magnetically stirred suspension of 1.00 g (2.62 mmol) of β-(3,3-diphenylpropyl)amino]benzenepropanol, monohydrochloride in 10 ml of p-dioxane was added 0.77 ml (5.50 mmol) of triethylamine followed by 0.41 ml (2.88 mmol) of benzyl chloroformate. After stirring for two hours, an additional 0.2 ml (1.40 mmol) of benzyl chloroformate was added. After stirring an additional two hours, the mixture was filtered through Celite and rotary evaporated. The residue was taken up in ethyl acetate and washed with 10% aqueous hydrochloric acid, 5% aqueous sodium bicarbonate, brine, dried over anhydrous magnesium sulfate, filtered and rotary evaporated leaving 1.39 g of the title compound as a yellow oil, used as is in the subsequent reaction.

(D) β-[[[(Phenylmethyl)oxy]carbonyl](3,3-diphenylpropyl)amino]benzenepropanal

To a magnetically stirred mixture of 1.39 g (2.90 mmol) of β-[[[(phenylmethyl)oxy]carbonyl](3,3-diphenylpropyl)amino]benzenepropanol 5.7 ml (47.9 mmol) of triethylamine and 8.5 ml of dimethylsulfoxide under argon was added dropwise a solution of 1.38 g (8.7 mmol) of pyridine.sulfur trioxide in 8.5 ml of dimethylsulfoxide. The mixture was then brought to pH 5 with concentrated hydrochloric acid and the mixture partitioned between ethyl acetate and water. The layers were separated and the ethyl acetate layer was washed repeatedly with water. The ethyl acetate layer was then dried over anhydrous magnesium sulfate, filtered and rotary evaporated. The residue was taken up in a minimum amount of ether and hexane was added until a cloudy appearance. Exhaustive washing with water followed by drying over anhydrous magnesium sulfate, filtration, and rotary evaporation gave 1.34 g of the title compound as a yellow oil, used as is in the subsequent reaction.

(E) (erythro)-β-[[[(Phenylmethyl)oxy]carbonyl](3,3-diphenylpropyl)amino]-α-methylbenzenepropanol To a magnetically stirred solution of 1.34 g (2.81 mmol) of β-[[[(phenylmethyl)oxy]carbonyl](3,3-diphenylpropyl)amino]benzenepropanal in 10 ml of tetrahydrofuran at 0° C. under argon was added 1.15 ml (2.6M in ether, 3.00 mmol) of methylmagnesium iodide. After allowing the mixture to warm to room temperature, it was quenched by the addition of 5 ml of saturated aqueous ammonium chloride. The mixture was then rotary evaporated and the residue partitioned between ethyl acetate and water. The ethyl acetate layer was then washed with 10% aqueous sodium bisulfite, water, brine, dried over magnesium sulfate, filtered and rotary evaporated. Flash chromatography (3:1 hexane:ethyl acetate) of the residue gave 0.68 g of the title compound as a yellow gum.

(F) (erythro)-β-[(3,3-Diphenylpropyl)amino]-α-methylbenzenepropanol, monohydrochloride A magnetically stirred mixture of 0.68 g (1.38 mmol) of (erythro)-β-[[[(phenylmethyl)oxy]carbonyl](3,3-diphenylpropyl)amino]-β-methylbenzenepropanol 0.07 g of 10% palladium on charcoal and 10 ml of methanol was allowed to stir under hydrogen overnight. The mixture was then filtered through Celite and the filtrate rotary evaporated. Flash chromatography of the residue (20:1 dichloromethane:methanol) followed by addition of an excess of 10% hydrochloric acid and rotary evaporation gave, after drying under high vacuum, 0.25 g of the title compound as a white solid foam, melting point 133°–134° C.

Analysis Calc'd for $C_{24}H_{29}NO \cdot HCl \cdot 0.2MH_2O$: C, 75.15; H, 7.67; N, 3.51; Cl, 8.87; Found: C, 75.17; H, 7.75; N, 3.44; Cl, 8.58.

EXAMPLE 2

β-[(3,3-Diphenylpropyl)amino]-3,4-dimethoxybenzenepropanol, monohydrochloride (A) α-[(1-Oxo-3,3-diphenylpropyl)amino]-3,4-dihydroxybenzenepropionic acid, methyl ester A mixture of 5.0 g of diphenylpropionic acid (22.1 mmole), 3.29 g of hydroxybenzotriazole (24.3 mmole), 5.01 g of dicyclohexylcarbodiimide (24.3 mmole), and 25 ml of dry tetrahydrofuran was allowed to stir at room temperature under argon for 1 hour. β-(3,4-Dihydroxyphenyl)-α-alanine, methyl ester, hydrochloride (5.47 g, 22.1 mmole) and 3.1 ml of triethylamine (22.1 mmole) was added to the mixture and allowed to stir overnight. The mixture was partitioned between water and ethyl acetate. The ethyl acetate layer was washed with 10% aqueous hydrochloric acid, 5% aqueous sodium bicarbonate, brine, dried over magnesium sulfate, filtered and evaporated at reduced pressure. Recrystallization from toluene afforded 6.68 g of the title compound as an off-white solid, melting point 161°–162° C.

(B) α-[(1-Oxo-3,3-diphenylpropyl)amino]-3,4-dimethoxybenzenepropionic acid, methyl ester A mixture of 6.0 g of α-[(1-oxo-3,3-diphenylpropyl)amino]-3,4-dihydroxybenzenepropionic acid, methyl ester (14.3 mmole), 1.8 1 ml of methyl iodide (29.0 mmole), 4.28 1 g potassium carbonate (31.0 mmole), and 65 ml of acetate was heated to reflux under argon overnight. The mixture was cooled and the solvent was removed in vacuo. The residue was taken up in ethyl acetate and washed with water, brine, dried over magnesium sulfate, filtered and evaporated at reduced pressure to afford 6.0 g of the title compound.

(C) α-[(1-Oxo-3,3-diphenylpropyl)amino]-3,4-dimethoxybenzenepropionic acid

α-[(1-Oxo-3,3-diphenylpropyl)amino]-3,4-dimethoxybenzenepropionic acid, methyl ester (6.0 g) in 1N sodium hydroxide, tetrahydrofuran, and methanol was allowed to stir at room temperature for several hours. The mixture was evaporated to 50% volume and poured into ethyl acetate and water. The layers were separated and the aqueous layer was brought to pH 2 using concentrated hydrochloric acid. The mixture was extracted with ethyl acetate (2×50 ml) and the combined extracts were washed with water, brine, dried over magnesium sulfate, filtered and evaporated at reduced pressure.

(D) β-[(3,3-Diphenylpropyl)amino]-3,4-dimethoxybenzenepropanol, monohydrochloride To 29.9 ml of magnetically stirred 1M boron trihydride.tetrahydrofuran complex (29.9 mmole) at 0° C. under argon was added portionwise 4.0 g of α-[(1-oxo-3,3-diphenylpropyl)amino]-3,4-dimethoxybenzenepropionic acid (9.96 mmole). After the addition and the cessation of hydrogen evolution, the solution was heated to reflux for 2 hours. The mixture was quenched with water, and the solvent was removed in vacuo. The residue was taken up in ethyl acetate and washed with 5% aqueous sodium bicarbonate, water, brine, dried over magnesium sulfate, filtered and rotary evaporated. The residue was taken into 1N hydrochloric acid, allowed to stir for 1 hour, and the mixture was rotary evaporated to yield 3.19 g of the title compound. The foam was triturated with isopropyl ether/hexane to yield 3.02 g of the title compound as a yellow glassy solid, melting point 181°–190° C. (becomes a gel).

Analysis Calc'd for $C_{26}H_{31}NO_3 \cdot HCl$: C, 70.8; H, 7.08; N, 3.18; Cl, 8.04; Found: C, 70.78; H, 7.39; N, 3.26; Cl, 7.94.

EXAMPLE 3

3-Methoxy-β-[(3,3-diphenylpropyl)amino]benzenepropanol (A) α-[(1-Oxo-3,3-diphenylpropyl)amino]acetic acid, ethyl ester A mixture of diphenylpropionic acid (0.44 moles, 100.0 g) in dichloromethane (1.5 L) at 0° C. under argon was treated with oxalyl chloride (0.44 mmole, 39 ml) and allowed to stir at 0° C. until gas evolution ceased. A solution of glycine ethyl ester hydrochloride (0.44 mmole, 61.7 g) in water (2.0 l) was added to the mixture and the pH was maintained at pH ~ 8. After 45 minutes, the pH stabilized, and the mixture was poured into a separatory funnel and the layers were separated. The organic layer was washed with brine, dried over anhydrous magnesium sulfate, filtered, and evaporated in vacuo. Recrystallization from toluene afforded 102.7 g of the title compound as a solid.

(B) α-[(1-Oxo-3,3-diphenylpropyl)amino]acetic acid, 1,1-dimethylethyl ester

α-[(1-Oxo-3,3-diphenylpropyl)amino]acetic acid, ethyl ester (0.16 mole, 50 g) was hydrolyzed in absolute ethanol (10 L) and 50% aqueous sodium hydroxide (20 ml). After 15 minutes, volume was reduced by 50% in vacuo, and the mixture was diluted with water (2 L), acidified to pH 2 with 6N aqueous hydrochloric acid, and extracted with ethyl acetate (2 times). The ethyl acetate layer was dried over anhydrous magnesium sulfate, filtered, and the solvent removed under reduced pressure to yield the free acid as a white solid (37.6 g). The free acid (37.6 g), dichloromethane (1.2 L), and concentrated sulfuric acid (5 ml) were allowed to stir in a flask. Isobutylene (300 ml) was condensed into the mixture and allowed to stir overnight as the isobutylene evaporated. The reaction mixture was poured into 1N anhydrous magnesium sulfate, filtered and evaporated in vacuo to yield an oil. Trituration with hexanes gave 37.6 g of the title compound as a white solid, melting point 77°–81° C.

(C) 1-(Chloromethyl)-2-methoxybenzene

Dimethoxybenzyl alcohol (151 mmole, 25.4 g) was poured into concentrated hydrochloric acid (200 ml). The white solid was extracted into ether and the organic layer was dried and evaporated to yield crude product. The solid was recrystallized from hexanes to afford 22.6 g of the title compound, melting point 69.5°–70.5° C.

(D) 3-Methoxy-α-[(1-oxo-3,3-diphenylpropyl)amino]benzenepropionic acid, 1,1-dimethylethyl ester Diisopropylamine (29.03 mmole, 4.1 ml), tetramethylenediamine (28.3 mmole, 3.6 ml), and tetrahydrofuran (70 ml) at 0° C. under argon was treated dropwise with n-butyllithium (28.3 mmole, 18.9 ml of 1M in hexane) and allowed to stir for 20 minutes. A solution of the α-[(1-oxo-3,3-diphenylpropyl)amino]acetic acid, 1,1-dimethylethyl ester (14.16 mmole, 5.0 g) was added dropwise to the lithium diisopropylamide at −78° C. and allowed to stir for 1 hour. Additional tetrahydrofuran (50 ml) was added.

A solution of 1-(chloromethyl)-2-methoxybenzene (14.16 mmole, 2.06 ml) in tetrahydrofuran (50 ml) was added to the yellow anion at −78° C. and allowed to stir overnight. The clear yellow solution was poured into 5% potassium bisulfate and the organic layer was saved. The potassium bisulfate layer was back extracted with ethyl acetate and the combined organic layers were washed with potassium bisulfate, sodium bicarbonate, brine, dried over anhydrous magnesium sulfate, filtered and evaporated in vacuo to yield a green oil. A yellow solid was obtained upon trituration with ether:-hexanes. The solid could not be recrystallized; flash chromatography (100 g LPS-1, 30% ethyl acetate/hexanes) yielded 0.53 g of the title compound as a white crystalline solid, melting point 111°–119° C.

(E) 3-Methoxy-β-[(3,3-diphenylpropyl)amino]benzenepropanol

3-Methoxy-α-[(1-oxo-3,3-diphenylpropyl)amino]benzenepropionic acid, 1,1-dimethylethyl ester (1 eq, 1 mmole, 470 mg) was added portionwise to a mixture of lithium aluminum hydride (3 mmole, 3 ml of 1M in tetrahydrofuran) in tetrahydrofuran (5 ml) at 0° C. under argon. After the addition and the cessation of hydrogen evolution, the mixture was brought to reflux. The mixture was refluxed overnight, cooled to room temperature and quenched with solid sodium sulfate.10 water. The solids were removed by filtration through Celite, and the solvent was evaporated in vacuo to yield an oil which crystallized upon standing. The crystals were washed with hexanes/ether, collected, and dried to afford 299.9 mg of the title compound, melting point 89°–91° C.

Analysis Calc'd for $C_{25}H_{29}NO_2$: C, 79.96; H, 7.78; N, 3.73; Found: C, 79.94; H, 7.83; N, 3.75.

EXAMPLE 4

β-[(3,3-Diphenylpropyl)amino]-2,5-dimethoxybenzenepropanol, oxalate salt (1:1)

(A) 2,5-Dimethoxy-α-[(1-oxo-3,3-diphenylpropyl)amino]benzenepropionic acid, 1,1-dimethylethyl ester A mixture of diisopropylamine (29.1 mmole, 4.1 ml), tetramethylenediamine (28.4 mmole, 3.6 ml), and tetrahydrofuran (72 ml) at −78° C. under nitrogen was treated dropwise with n-butyllithium (28.4 mmole, 18.9 ml). The mixture was stirred for 20 minutes. A solution of α-[(1-oxo-3,3-diphenylpropyl)amino]acetic acid, 1,1-dimethylethyl ester (14.2 mmole, 5 g; see example 3B) in tetrahydrofuran (30 lm) was added dropwise to the mixture of lithium diisopropylamide at −78° C. and stirred for 1 hour. The gelatinous dianion solution was quenched with a solution of 2,5-dimethoxy benzylchloride (14.2 mmole, 2.6 g) in tetrahydrofuran (5 ml) and the mixture warmed to room temperature as it stirred overnight. The mixture was poured into 10% aqueous potassium bisulfate, and the aqueous layer was separated and extracted with ethyl acetate. The combined organic layers were washed with potassium bisulfate, saturated aqueous sodium bicarbonate and brine. Drying over anhydrous magnesium sulfate, filtering, and removing solvent in vacuo yielded a green oil. Flash chromatography (1:2 ethyl acetate:hexanes, 650 g LPS-1 silica) yielded a green oil. A second flash chromatography (50% ether/hexane, 300 g LPS-1 silica) yielded an oil which solidified upon trituration with ether to a white solid, melting point 124.5°–125° C.

(B) β-[(3,3-Diphenylpropyl)amino]-2,5-dimethoxybenzenepropanol, oxalate salt (1:1)

2,5-Dimethoxy-α-[(1-oxo-3,3-diphenylpropyl)amino]benzenepropionic acid, 1,1-dimethylethyl ester (2.55 mmole, 1.25 g) was added portionwise to a solution of lithium aluminum hydride (7.65 mmole, 7.65 ml of 1M in tetrahydrofuran in anhydrous tetrahydrofuran at 0° C. under nitrogen. After the addition and the cessation of gas evolution, the mixture was warmed to reflux and stirred overnight. The mixture was quenched with sodium sulfate.10 water, salted with sodium chloride, filtered and evaporated in vacuo to yield a clear colorless oil. The oil was dissolved in isopropylalcohol and oxalic acid (0.8M in isopropanol, 3.9 ml) was added dropwise to the solution at 0° C. with stirring. A white solid formed which went into solution. Ether was added, and the mixture was placed in the freezer overnight. The solid was collected by filtration to obtain a white powder. Recrystallization from a minimal amount of methanol afforded the title compound as a white crystalline solid, melting point 171.5°–172° C.

Analysis Calc'd for $C_{26}H_{31}NO_3 \cdot C_2H_2O_4$: C, 67.9; H, 6.71; N, 2.83; Found: C, 67.88; H, 6.79; N, 2.74.

EXAMPLE 5

(DL-erythro)-β-[(3,3-Diphenylpropyl)amino]-2,5-dimethoxy-α-methylbenzenepropanol, oxalate salt (1:1)

(A) β-[[[(Phenylmethyl)oxy]carbonyl](3,3-diphenylpropyl)amino]-2,5-dimethoxybenzenepropanol To a magnetically stirred solution of (DL-erythro)-β-[(3,3-diphenylpropyl)amino]-2,5-dimethoxy-α-methylbenzenepropanol, oxalate salt (1:1) (3.26 mmole, 1.32 g; see example 5) and triethylamine (3.26 mmole, 0.45 ml) in p-dioxane (12.5 ml) at room temperature under nitrogen was added benzyl chloroformate (1.2 eq, 3.91 mmole, 0.6 ml). The mixture was stirred overnight, filtered and the filtrate was evaporated in vacuo. The residue was taken into ethyl acetate and washed with 1N aqueous hydrochloric acid, saturated aqueous sodium bicarbonate, brine, dried over anhydrous magnesium sulfate, filtered, and evaporated. Flash chromatography of the green syrup (1:2 :ethyl acetate:hexane, 175 g LPS-1 silica) afforded 924.5 mg of the title compound as an oil.

(B) β-[[[(Phenylmethyl)oxy]carbonyl](3,3-diphenylpropyl)amino]-2,5-dimethoxybenzenepropanol To a magnetically stirred mixture of β-[[[(phenylmethyl)oxy]carbonyl](3,3-diphenylpropyl)amino]2,5-dimethoxybenzenepropanol (1.71 mmole, 924 mg) and N,N-diisopropylethylamine (28.2 mmole, 4.9 ml) in dimethylsulfoxide (4 ml) at room temperature under nitrogen was added fresly prepared pyridine.sulfur trioxide complex (3 eq, 5.13 mmole, 816.5 mg) in dimethylsulfoxide (4.5 ml). After 30 minutes, the mixture was poured into water (60 ml) and extracted with ether (3×40 ml). The ether layers were combined and washed with citric acid (3×40 ml), saturated aqueous sodium bicarbonate (3×40 ml), water (10×30 ml) and brine. The water layers were combined and back extracted with ether. The combined ether layers were dried over anhydrous magnesium sulfate, filtered and stripped to afford 610 mg of an oil.

(C) (DL-erythro)-β-[[[(Phenylmethyl)oxy]carbonyl](3,3-diphenylpropyl)amino]-2,5-dimethoxy-α-methylbenzenepropanol To a magnetically stirred solution of methylmagnesium iodide (1.42 mmole, 0.5 ml) in tetrahydrofuran (0.5 ml) at 0° C. under nitrogen was added a solution of β-[[[(phenylmethyl)oxy]carbonyl](3,3-diphenylpropyl)amino]-2,5-dimethoxybenzenepropanol (1.18 mmole, 635 mg) in tetrahydrofuran (3.5 ml). After 1 hour, the reaction was quenched with 2 ml of saturated aqueous ammonium chloride and the layers were separated. The aqueous layer was back extracted with ether and the combined organic layers were washed with saturated aqueous sodium bicarbonate, brine, dried over magnesium sulfate, filtered and stripped in vacuo to yield an oil. Flash chromatography (1:3, ethyl acetate:hexane, 40 g LPS-1 silica) yielded 428 mg of the title compound as an oil.

(D) (DL-erythro)-β-[(3,3-Diphenylpropyl)amino]-2,5-dimethoxy-α-methylbenzenepropanol oxalate salt (1:1)

(DL-erythro)-β-[[[(Phenylmethyl)oxy]carbonyl](3,3-diphenylpropyl)amino]-2,5-dimethoxy-α-methylbenzenepropanol (215 mg, 0.4 mmole) was hydrogenated in methanol (3 ml) over Pearlman's catalyst (15% by weight, 32.3 mg) overnight. The mixture was filtered through Celite and evaporated in vacuo to yield an oil. The oil was taken into isopropyl alcohol and 0.88M oxalic acid in isopropylalcohol (0.5 ml) was added. The white oxalate salt dropped out and was collected by filtration and washed with ether. The mother liquor was evaporated in vacuo and 0.88M oxalic acid solution (0.5 ml) was added. The product was again collected by filtration and washed with ether.

Crop 1–75 mg, melting point 201.5°–202.5° C.
Crop 2–24.3 mg, melting point 201.5°–202.5° C.
Recrystallization from methanol yielded 70 mg of product, melting point 205°–205.5° C.

Analysis Calc'd for $C_{27}H_{34}NO_3.0.5M\ C_2H_2O_4$: C, 72.39; H, 7.38; N, 3.01; Found: C, 72.46; H, 7.39; N, 2.73.

EXAMPLE 6

(erythro)-β-[(3,3-Diphenylpropyl)amino]-3,4-dimethoxy-α-methylbenzenepropanol, oxalate salt (1:1)

(A) β-[[[(Phenylmethyl)oxy]carbonyl](3,3-diphenylpropyl)amino]-3,4-dimethoxybenzenepropanol To a magnetically stirred solution of β-[(3,3-diphenylpropyl)amino]-3,4-dimethoxybenzenepropanol, monohydrochloride (3.66 mole, 1.62 g; see example 2) and triethylamine (7.32 mmole, 1.02 ml) in p-dioxane (14 ml) at room temperature under nitrogen was added benzyl chloroformate (4.39 mmole, 0.63 ml). The reaction was complete in 4 hours. The mixture was filtered and the filtrate reduced in vacuo to yield an oil. The oily residue was taken into ethyl acetate and washed with 1N aqueous hydrochloric acid, saturated aqueous sodium bicarbonate, brine, dried over magnesium sulfate, filtered and evaporated. Flash chromatography (160 g of LPS-1 silica, 1:1 ethyl acetate:hexane, eluted ~50 ml/min.) afforded 1.28 g of the title compound as an oil.

(B) β-[[[(Phenylmethyl)oxy]carbonyl](3,3-diphenylpropyl)amino]-3,4-dimethoxybenzenepropanol To a magnetically stirred mixture of β-[[[(phenylmethyl)oxy]carbonyl](3,3-diphenylpropyl)amino]-3,4-dimethoxybenzenepropanol (2.28 mmole, 1.23 g) and N,N-diisopropylethylamine (13.68 mmole, 2.38 ml) in dimethylsulfoxide (7.4 ml) at room temperature under nitrogen was added freshly prepared pyridine.sulfur trioxide (6.84 mmole, 1.1 g) in dimethylsulfoxide (4 ml). The mixture was poured into water (10 ml) and ether (20 ml) and the layers were separated. The aqueous layer was extracted with ether (3×5 ml). The combined ether layers were washed with water (2×10 ml, 8×5 ml), the combined aqueous washes were back extracted with ether (2×10 ml) and all organic layers were combined. The ether layer was washed with aqueous citric acid (3×5 ml), saturated aqueous sodium bicarbonate (1×5 ml), and brine, dried over anhydrous magnesium sulfate, filtered, and reduced in vacuo to yield 1.1 g of an oil.

(C) (erythro)-β-[[[(Phenylmethyl)oxy]carbonyl](3,3-diphenylpropyl)amino]-3,4-dimethoxy-α-methylbenzenepropanol A solution of β-[[[(phenylmethyl)oxy]carbonyl](3,3-diphenylpropyl)amino]-3,4-dimethoxybenzenepropanol in dry tetrahydrofuran (7 ml) was added to methylmagnesium bromide (2.54 mmole, 0.89 ml) in tetrahydrofuran (3 ml) at 0° C. under nitrogen. After 1 hour, additional Grignard (0.15 ml) was added. After 30 minutes, some faint by-products appeared in addition to starting material. The mixture was quenched with saturated aqueous ammonium chloride and layers were separated. The aqueous layer was back extracted with ether and the organic layers were combined and washed with water (2×5, 8×2), the combined aqueous washes were back extracted with ether and the two ether layers combined. The organic layer was washed with 5% aqueous citric acid, saturated aqueous sodium bicarbonate, and brine, dried over anhydrous magnesium sulfate, filtered, and evaporated in vacuo to yield an oil. Flash chromatography (1:2 ethyl acetate:hexane, 80 g LPS-1 silica) yielded 710 mg of the title compound as an oil.

(D) (erythro)-β-[(3,3-Diphenylpropyl)amino]3,4-dimethoxy-α-methylbenzenepropanol, oxalate salt (1:1)

(erythro)-β-[[[(Phenylmethyl)oxy]carbonyl](3,3-diphenylpropyl)amino]-3,4-dimethoxy-α-methylbenzenepropanol (300 mg, 0.54 mmole) was hydrogenated over palladium on charcoal (45 mg) in methanol (3 ml) at atmospheric pressure overnight. The mixture was filtered through Celite and evaporated in vacuo to yield an oil. The oil was dissolved in isopropyl alcohol and treated with 0.8M oxalic acid/isopropanol solution. The white solid was collected by filtration and the mother liquor evaporated and redissolved in the oxalic acid/isopropanol solution. No additional solids were collected. The yield of product was 77.0 mg, melting point 147°–150° C.

Analysis Calc'd for $C_{27}H_{33}NO_3.0.1MC_2H_2O_4$: C, 68.25; H, 7.00; N, 2.72; Found: C, 67.86; H, 7.38; N, 2.47.

EXAMPLE 7

(threo)-β-[(3,3-Diphenylpropyl)amino]-3,4-dimethoxy-α-methylbenzenepropanol, oxalate salt (1:1)

(A) 2-[[[(Phenylmethyl)oxy]carbonyl](3,3-diphenylpropyl)amino]-(3,4-dimethoxybenzene)butan-3-one A solution of pyridine.sulfur trioxide (2.19 mmole, 0.35 g) in dimethylsulfoxide (1 ml) was added dropwise with stirring to a mixture of (erythro)-β-[[[(phenylmethyl)oxy]carbonyl](3,3-diphenylpropyl)amino]-3,4-dimethoxy-α-methylbenzenepropanol (0.73 mmole, 404 mg; see example 6C), diisopropylethylamine (4.4 mmole, 0.77 ml) and dimethylsulfoxide (3 ml) at room temperature under nitrogen. After 20 minutes, the mixture was poured into ether (8 ml) and water (4 ml) and the layers were separated. The aqueous layer was extracted with ether (2×2 ml) and the combined organic layers were washed repeatedly with water (10×2 ml), 5% citric acid (2×5 ml), and saturated aqueous sodium bicarbonate (1×5 ml). The ether layer was dried with brine and magnesium sulfate, filtered and evaporated in vacuo to afford 292.3 mg of the product as a foam.

(B) (threo)-β-[[[(Phenylmethyl)oxy]carbonyl](3,3-diphenylpropyl)amino]-3,4-dimethoxy-α-methylbenzenepropanol Sodium borohydride (0.13 mmole, 4.9 mg) was added in one portion to a solution of 2-[[[(phenylmethyl)oxy]carbonyl](3,3-diphenylpropyl)amino](3,4-dimethoxybenzene)butan-3-one (0.53 mmole, 292 mg) in methanol (2.5 ml) at room temperature under nitrogen. The mixture was quenched with 1N hydrochloric acid and partitioned between water and ethyl acetate. The aqueous layer was extracted with ethyl acetate (2×10 ml), dried over magnesium sulfate, filtered, and evaporated in vacuo to yield an oil. Flash chromatography (30 g LPS-1 silica, 1:2 ethyl acetate:hexane) isolated the product as a foam (234 mg).

(C) (threo)-β-[(3,3-Diphenylpropyl)amino]-3,4-dimethoxy-α-methylbenzenepropanol, oxalate salt (1:1)

(threo)-β-[[[(Phenylmethyl)oxy]carbonyl](3,3-diphenylpropyl)amino]-3,4-dimethoxy-α-methylbenzenepropanol (0.39 mmole, 214 mg) in methanol (2 ml) was hydrogenated over palladium on charcoal (32 mg) overnight. The mixture was filtered through Celite and evaporated in vacuo to yield an oil (164.5 mg).

The oil was taken into isopropanol and treated with oxalic acid (0.33 mmole, 0.66 ml as 0.5M solution in isopropanol). The white solid was collected by filtration, and recrystallization from methanol to afford pure product as a white crystalline solid (104 mg, melting point 155°–158° C.).

Analysis Calc'd for $C_{27}H_{33}NO_3 \cdot C_2H_4O_4$: C, 68.34; H, 6.92; N, 2.75; Found: C, 68.04; H, 7.04; N, 2.53.

EXAMPLE 8

β-[(3,3-Dicyclohexylpropyl)amino]-2,5-dimethoxybenzenepropanol, maleate salt (1:1)

(A) 3,3-Dicyclohexylpropionic acid

A solution of 15 g (0.066 mol) of 3,3-diphenylpropionic acid in 200 ml of acetic acid was treated with 2.25 g of platinum oxide and shaken on the Parr hydrogenator for 24 hours at a starting pressure of 60 lbs. Whenever the pressure dropped to approximately 45 lbs., the system was repressurized to 60 lbs. After heating on the steam bath to redissolve solid which had separated, the solution was decanted from the catalyst which had settled, filtered under argon, and the catalyst washed with additional acetic acid by decantation. The acetic acid was removed on a rotary evaporator to give a colorless solid (remaining acetic acid azeotroped with toluene). The solid was taken up in 250 ml of chloroform, filtered to clarify, and the chloroform evaporated. The product was suspended in ether and the evaporation repeated. After drying at reduced pressure for 2 hours, the solid weighed 15.25 g, melting point 118°–120° C. (s, 114° C.).

(B) 3,3-Dicyclohexylpropionyl chloride

A stirred solution of 3,3-dicyclohexylpropionic acid (15.2 g, 0.064 mol) in 225 ml of dichloromethane was cooled to 5° C. and treated with 6.8 ml (0.078 mol) of oxalyl chloride, followed by 10 drops of dimethylformamide. The cooling bath was removed and stirring was continued at room temperature. Gas evolution, which was vigorous initially, essentially ceased after 1 hour. After 3 hours, dichloromethane and excess oxalyl chloride were removed on a rotary evaporator. The residue was taken up in dichloromethane and the evaporation was repeated to give 16.1 g of a pale yellow oil.

(C) α-[(1-Oxo-3,3-dicyclohexylpropyl)amino]acetic acid, 1,1-dimethylethyl ester

A stirred solution of 3,3-dicyclohexylpropionyl chloride (6.1 g, 0.063 mol) in 70 ml of chloroform was treated portionwise at 7°–12° C. with a solution of 8.3 g (0.063 mol) of glycine tert-butyl ester and 8.9 ml (0.064 mol) of triethylamine in 30 ml of chloroform. After the addition, the solution was stirred at room temperature for 2 hours, kept overnight, refluxed for 0.5 hours, cooled, washed with water (5×25 ml), dried (magnesium sulfate), and the solvent removed on a rotary evaporator, to give a light yellow viscous oil. The latter, which crystallized partly on standing, was dissolved in 50 ml of boiling hexane, cooled, seeded, and rubbed; a crystalline solid gradually separated. After crystallizing at room temperature and cooling overnight, the voluminous colorless solid was filtered, washed with cold hexane and air-dried (13.3 g, melting point 72°–74° C. s, 69° C.).

(D) α-[(1-Oxo-3,3-dicyclohexylpropyl)amino]-2,5-dimethoxybenzenepropionic acid, 1,1-dimethylethyl ester The following procedure was carried out under argon. A stirred solution of 4.1 ml (29.2 mmol) of diisopropylamine and 4.3 ml (28.5 mmol) of tetramethylenediamine in 75 ml of tetrahydrofuran was cooled to −75° C. and treated portionwise with 18 ml (28.4 mmol) of 1.6M n-butyllithium in hexane. After stirring for 20 minutes, α-[(1-oxo-3,3-dicyclohexylpropyl)amino]acetic acid, 1,1-dimethylethyl ester (5.0 g; 14.2 mmol) in 30 ml of tetrahydrofuran was added dropwise at −75° C. The color changed from nearly colorless to yellow. Stirring at −75° C. was continued for 1 hour, after which the gelatinous dianion solution was treated portionwise with 2.65 g (14.2 mmol) of 2,5-dimethoxybenzyl chloride in 10 ml of tetrahydrofuran. After stirring at −75° C. for 1 hour, the mixture was allowed to warm gradually to room temperature. The color lightened to pale yellow. After stirring overnight, the mixture was poured with stirring into 100 ml of crushed ice and 100 ml of 10% potassium bisulfate, ethyl acetate (50 ml) was added, the mixture shaken, and the layers separated. Since the aqueous phase was still basic, additional 10% potassium bisulfate was added (2×10 ml), followed by shaking, until the pH was approximately 6. The aqueous layer was then extracted with ethyl acetate (3×50 ml) and the combined organic layers washed with 40 ml each of 5% potassium bisulfate, water, and saturated sodium chloride solution. After drying (magnesium sulfate), the solvents were evaporated to give 7.6 g of a light yellow, mostly solid residue. The latter was ground in a mortar under 40 ml of ether, kept 3 hours at room temperature, cooled for 0.75 hours, and the colorless solid filtered, washed with 20 ml of cold ether, and air-dried (3.4 g; melting point 108°–111° C. s, 103° C.). Following crystallization from 45 ml of isopropyl ether, the product weighed 2.9 g, melting point 114°–116° C.

(E) β-[(3,3-Dicyclohexylpropyl)amino]-2,5-dimethoxybenzenepropanol, maleate salt (1:1)

The following procedure was carried out under argon. α-[(1-Oxo-3,3-dicyclohexylpropyl)amino]-2,5-dimethoxybenzenepropionic acid, 1,1-dimethylethyl ester (2.85 g; 5.7 mmol) in 25 ml of tetrahydrofuran was added portionwise to a stirred suspension of 0.7 g (18.4 mmol) of lithium aluminum hydride in 100 ml of tetrahydrofuran; there was a slight temperature rise to 28° C.

After the addition, the mixture was stirred at room temperature for 1 hour, refluxed for 2 hours, and kept overnight at room temperature.

The mixture was stirred vigorously, cooled in ice water, and treated portionwise with 0.9 ml of water, followed by 3 ml of 15% sodium hydroxide. After stirring at room temperature for 45 minutes, the solids were filtered, washed well with tetrahydrofuran and ether, and the combined filtrates dried (magnesium sulfate). The solvents were removed on a rotary evaporator to give 2.7 g of a viscous syrup which began to crystallize on standing. Crystallization (of 2.6 g) from 15 ml of boiling isopropyl ether (crystalline solid separated rapidly) gave 1.58 g of colorless solid, melting point 77°–79° C. s. 74° C. (the free base of the title compound).

Analysis Calc'd for $C_{26}H_{43}NO_3.0.2H_2O$: C, 73.97; H, 10.39; N, 3.32; Found: C, 74.16; H, 10.12; N, 2.81.

Since the hydrochloric acid salt was an oil, the solid maleate salt was prepared. The base (1.51 g) in 10 ml of warm isopropanol was treated with 0.43 g of maleic acid and while still warm diluted to 75 ml with ether; the solid maleate salt rapidly separated. After cooling overnight, the colorless solid was filtered, washed with ether, and dried in vacuo (1.44 g; melting point 141°–143° C.). Following recrystallization (of 1.42 g) from 12 ml of acetonitrile, the product weighed 1.37 g, melting point 141°–143° C.

Analysis Calc'd for $C_{26}H_{43}NO_3.C_4H_4O_4$: C, 67.51; H, 8.88; N, 2.62; Found: C, 67.59; H, 8.71; N, 2.54.

Additional compounds which can be prepared utilizing the methodology illustrated in the above examples are:

β-[(3,3-dicyclohexylpropyl)amino]-2,5-dimethoxy-α-methylbenzenepropanol (erythro and threo isomers)

β-[(3,3-dicyclohexylpropyl)(methyl)amino]-2,5-dimethoxy-α-methylbenzenepropanol (erythro and threo isomers)

β-[(3,3-dicyclohexylpropyl)amino]-3,4-dimethoxy-α-methylbenzenepropanol (erythro and threo isomers)

β-[(3,3-dicyclohexylpropyl)amino]-3,4-dimethyl-α-methylbenzenepropanol (erythro and threo isomers)

β-[[3,3-bis(4-fluorophenyl)propyl]amino]-2,5-dimethoxy-α-methylbenzenepropanol (erythro and threo isomers)

β-[(3,3-dicyclohexylpropyl)amino]-4-methoxy-α-methylbenzenepropanol (erythro and threo isomers)

β-[(3,3-dicyclohexylpropyl)amino]-3-methoxy-α-methylbenzenepropanol (erythro and threo isomers)

β-[(3,3-dicyclopentylpropyl)amino]-2,5-dimethoxy-α-methylbenzenepropanol (erythro and threo isomers)

β-[(3,3-dicyclopentylpropyl)amino]-3,4-dimethoxy-α-methylbenzenepropanol (erythro and threo isomers)

What is claimed is:

1. A compound having the formula

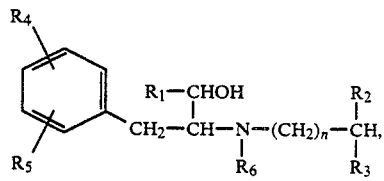

or a pharmaceutically acceptable salt thereof, wherein
$R_1$ is hydrogen or alkyl;
$R_2$ and $R_3$ are each independently cycloalkyl;
$R_4$ and $R_5$ are the same or different and each is hydrogen, hydroxy, alkoxy, alkanoyl or alkyl;
$R_6$ is hydrogen or alkyl; and
n is 1, 2, 3 or 4.

2. A compound in accordance with claim 1 wherein $R_1$ is hydrogen.

3. A compound in accordance with claim 1 wherein $R_1$ is alkyl.

4. A compound in accordance with claim 1 wherein $R_6$ is hydrogen.

5. A compound in accordance with claim 1 wherein $R_6$ is alkyl.

6. A compound in accordance with claim 1 wherein $R_4$ and $R_5$ are each hydroxy.

7. A compound in accordance with claim 1 wherein $R_4$ and $R_5$ are each methoxy.

8. A compound in accordance with claim 1 wherein n is 1.

9. A compound in accordance with claim 1 wherein n is 2.

10. A compound in accordance with claim 1 wherein n is 3.

11. A compound in accordance with claim 1 wherein n is 4.

12. The compound in accordance with claim 1, β-[(3,3-dicyclohexylpropyl)amino]-2,5-dimethoxybenzenepropanol or a salt thereof.

* * * * *